United States Patent

Hada et al.

[11] Patent Number: 5,879,648
[45] Date of Patent: Mar. 9, 1999

[54] APPARATUS FOR DISINFECTING CONTAINERS

[75] Inventors: Hiroaki Hada; Tadao Akai; Kazuo Abe; Hiroshi Kitajima; Michio Ueda, all of Tokushima, Japan

[73] Assignee: Shikoku Kakoki Co., Ltd., Tokushima, Japan

[21] Appl. No.: 955,243

[22] Filed: Oct. 21, 1997

[30] Foreign Application Priority Data

Oct. 23, 1996 [JP] Japan ................................ 8-280552

[51] Int. Cl.⁶ ...................................................... A61L 2/16
[52] U.S. Cl. ........................... 422/304; 422/28; 422/305; 422/307; 422/302
[58] Field of Search .................... 422/28, 32, 305, 422/307, 292, 300, 302, 304

[56] References Cited

U.S. PATENT DOCUMENTS

| 4,309,302 | 1/1982 | Tenney et al. ........................... 422/302 |
| 4,533,515 | 8/1985 | Witter et al. ............................ 422/304 |
| 4,742,667 | 5/1988 | Muller et al. ............................ 422/304 |
| 5,258,162 | 11/1993 | Andersson et al. ..................... 422/302 |

FOREIGN PATENT DOCUMENTS 63-11163   1/1988   Japan .

*Primary Examiner*—Krisanne Thornton
*Assistant Examiner*—Fariborz Moazzam
*Attorney, Agent, or Firm*—Armstrong, Westerman, Hattori, McLeland & Naughton

[57] ABSTRACT

An apparatus for disinfecting containers comprises a disinfection chamber 12 surrounding a required section of a container transport path, partition means for dividing the interior of the disinfection chamber 12 into a preheating zone 35, an exposure zone 36 and a drying zone 37 as arranged downstream from an upstream side of the transport path, antiseptic supply means for supplying hydrogen peroxide gas or mist to the exposure zone 36, and means for supplying hot air to the preheating zone 35 and the drying zone 37.

2 Claims, 3 Drawing Sheets

APPARATUS FOR DISINFECTING CONTAINERS

BACKGROUND OF THE INVENTION

The present invention relates to an apparatus for and a method of disinfecting containers, and to a method of disinfecting a packaging material for preparing the containers.

As disclosed, for example, in JP-A No. 63-11163, such an apparatus already known for disinfecting containers comprises a disinfection chamber surrounding a required section of a container transport path, partition means for forming inside the chamber an exposure zone positioned upstream with respect to the path and a drying zone downstream from the exposure zone, antiseptic supply means for supplying hydrogen peroxide gas to the exposure zone, and means for supplying hot air to the drying zone.

The apparatus described requires a large quantity of hot air for drying and removing the hydrogen peroxide adhering to containers with a stream of hot air. For this purpose, there is a need to retain the container within the drying zone for a predetermined period of time during transport, entailing a tendency for the drying zone to have an increased length. The packaging machine including the container disinfecting apparatus then becomes large-sized in its entirety to result in a higher cost.

SUMMARY OF TEE INVENTION

An object of the present invention is to provide an apparatus for disinfecting containers which has a drying zone of shortened length to compact the entire packaging machine including the disinfecting apparatus.

Another object of the invention is to provide a method of disinfecting a packaging material for preparing containers so that the material can be disinfected by the compacted apparatus.

The present invention provides an apparatus for disinfecting containers which comprises a disinfection chamber surrounding a required section of a container transport path, partition means for dividing the interior of the disinfection chamber into a preheating zone, an exposure zone and a drying zone as arranged downstream from an upstream side of the transport path, antiseptic supply means for supplying hydrogen peroxide gas to the exposure zone, and means for supplying hot air to the preheating zone and the drying zone.

With the apparatus of the invention which includes means for supplying hot air to the drying zone, the partition means forms inside the disinfection chamber a preheating zone upstream from the exposure zone, and the hot air supplying means is adapted to supply hot air to the preheating zone, so that containers are preheated before hydrogen peroxide is applied to thereto. This permits the hydrogen peroxide to achieve an improved disinfection effect, diminishing the amount of hydrogen peroxide to be applied to the container. Since the preheated container is transported to the drying zone, the hydrogen peroxide adhering to the container can be dried and removed with hot air even if the drying zone is shortened in length. Consequently, the packaging machine including the container disinfecting apparatus can be compacted in its entirety.

When the drying zone and the preheating zone are each maintained at a higher internal pressure than the exposure zone in the apparatus described, air is caused to flow out from the drying zone and the preheating zone toward the exposure zone. This eliminates the likelihood that the gas or mist of hydrogen peroxide will flow out from the exposure zone, obviating the adverse influence to be otherwise exerted on the human body or the environment.

The invention also provides a method of disinfecting a packaging material for containers which method comprises preheating the packaging material in the form of a sheet or as formed into containers, applying hydrogen peroxide gas to the preheated packaging material to cause hydrogen peroxide to condense on a surface of the packaging material, and drying and removing the hydrogen peroxide condensate on the surface of the packaging material with hot air.

Preferably, the packaging material has a polyethylene layer over the surface thereof and is preheated to a surface temperature of 40 to 80 deg C.

If the surface temperature is lower than 40 deg C., the disinfection effect of hydrogen peroxide on the surface will be low, whereas if the temperature exceeds 80 deg C., the polyethylene surface layer is likely to soften.

The hydrogen peroxide gas may be replaced by a mist of hydrogen peroxide. In this case the preheating temperature need not always be at least 40 deg C.

It is desired that the mist of hydrogen peroxide to be supplied to the exposure zone or to be sprayed on the packaging material be up to 100 micrometers in particle size.

If exceeding 100 micrometers in particle size, the mist requires a longer period of time for drying and will not be removed efficiently.

DESCRIPTION OF THE PREFERRED EMBODIMENTS

Embodiments of the invention will be described below with reference to the drawings.

Figure 1:
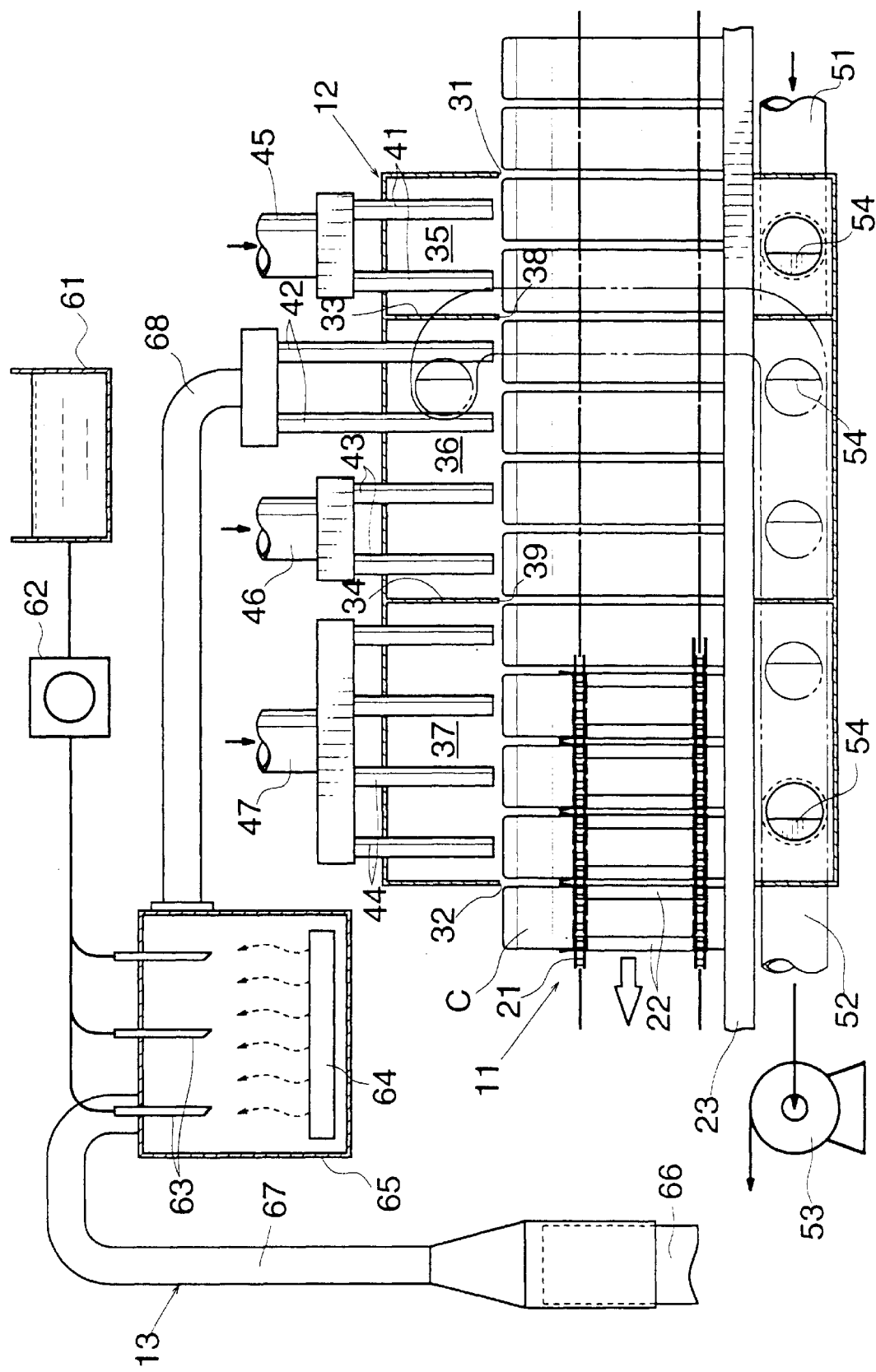
FIG. 1 is a side elevation showing a disinfecting apparatus embodying the invention.
Figure 2:
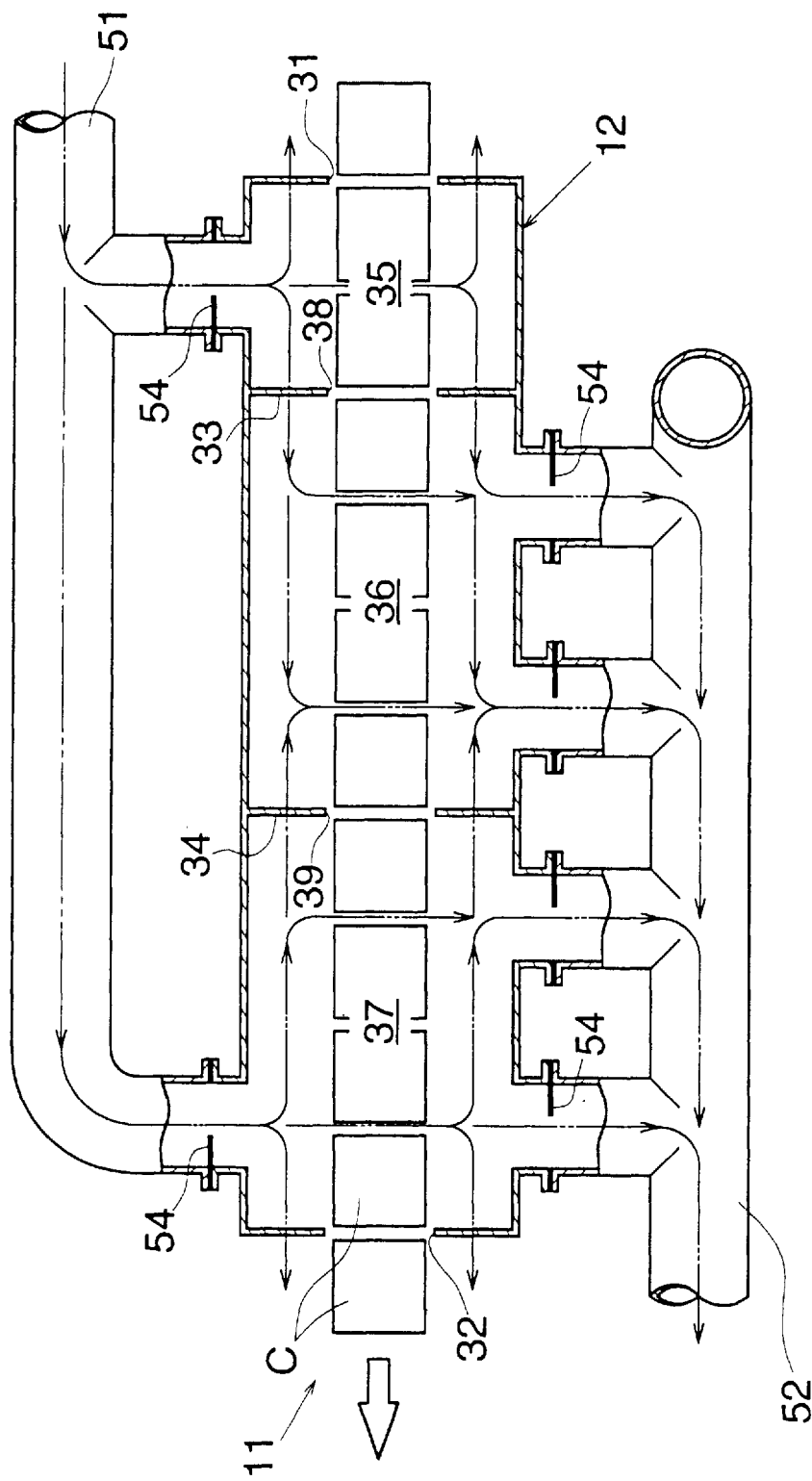
FIG. 2 is a plan view of the apparatus.

In the following description, the term "front" refers to the direction in which containers are transported by the conveyor (i.e., the left-hand side of FIG. 1), and the "rear" to the opposite direction. The terms "left" and "right" are used for the apparatus as it is seen from behind toward the front.

The drawings show a container disinfecting apparatus, which comprises a conveyor 11 for transporting containers C along a specified path, a disinfection chamber 12 surrounding a required section of the transport path of the conveyor 11, and a device 13 for supplying an antiseptic to the chamber 12.

Each container C is in the form of a tube having a bottom and a square to rectangular cross section, and is prepared from a packaging material of paper-base laminate having a polyethylene layer over the inner and outer surfaces thereof.

The conveyor 11, which is a chain conveyor, comprises intermittently drivable endless chains 21, holders 22 attached to the chains 21 at a predetermined interval and each comprising four vertical pieces which are L-shaped in cross section and which are to be fitted to the respective four corners of the container C, and a horizontal rail 23 for supporting the container C at its bottom for guiding. Containers C are transported simultaneously a distance at a time when the chains are driven one cycle which distance corresponds to two containers C as arranged along the path.

Figure 3:
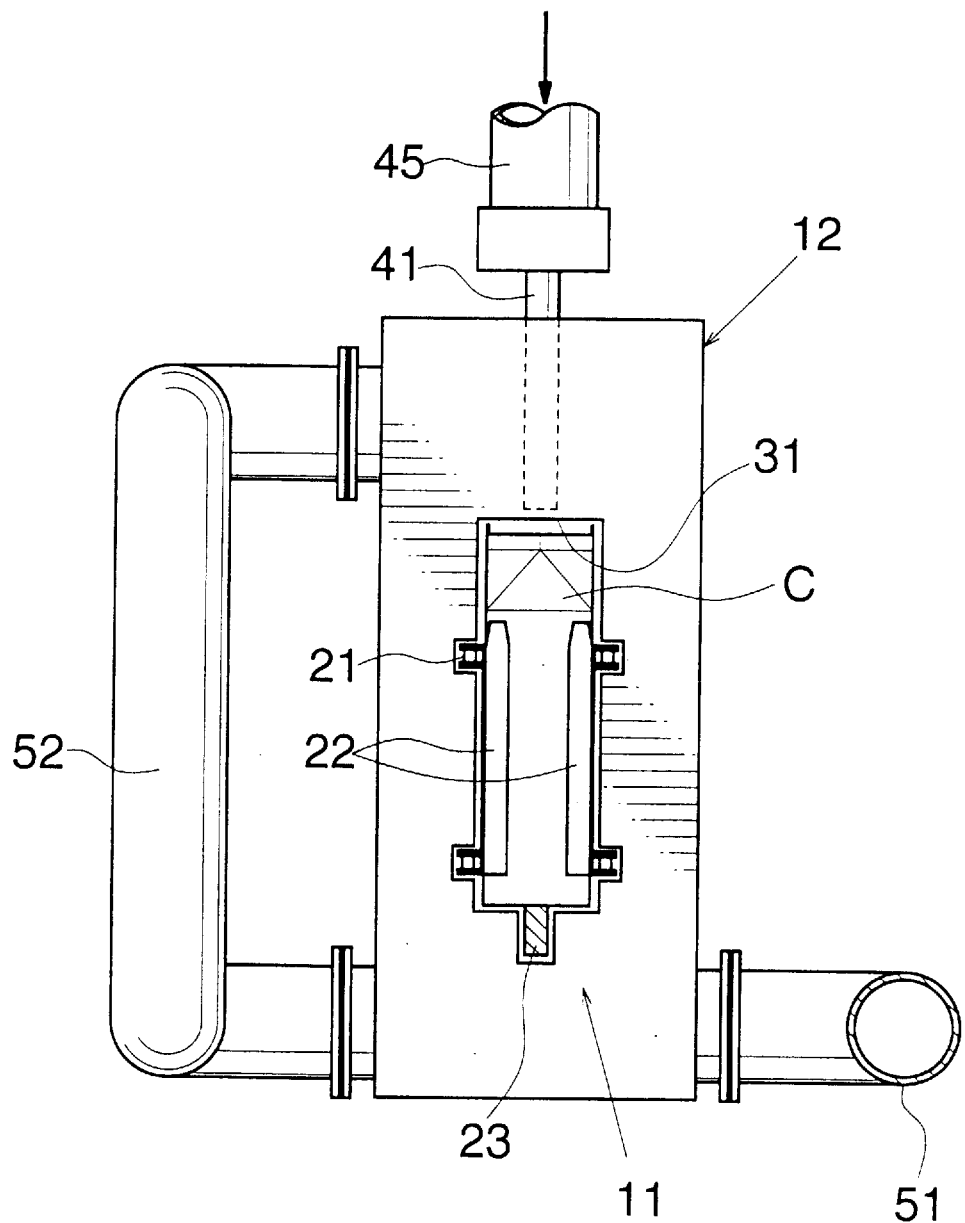
FIG. 3 is a rear view of the apparatus.

The disinfection chamber 12 is in the form of a closed box having a vertically elongated rectangular cross section, and has a container inlet 31 in its rear end wall and a container outlet 32 in its front end wall. As shown in FIG. 3, the inlet 31 and the outlet 32 are each an opening for passing the container C and the conveyor 11 with a very small clearance formed therearound. (The inlet 31 only is shown in FIG. 3.)

The disinfection chamber 12 is provided in its interior with a rear vertical partition 33 and a front vertical partition 34, whereby the interior of the chamber 12 is divided into a preheating zone 35, exposure zone 36 and drying zone 37 as arranged from the rear forward. The rear and front partitions 33, 34 are formed with container passage openings 38, 39, respectively, which are identical with the inlet 31 or outlet 32 in shape.

Two containers C are positioned as halted within the preheating zone 35, and four containers C within each of the exposure zone 36 and the drying zone 37.

Two preheating hot air nozzles 41 are arranged in the preheating zone 35. These nozzles 41 extend through the top wall of the preheating zone 35 and have their lower-end spouts opposed to the top openings of the two respective containers C as halted at two respective stop positions. The exposure zone 36 is provided with two hydrogen peroxide gas nozzles 42 and two predrying hot air nozzles 43. The two gas nozzles 42 correspond to two upstream positions among four container stop positions in the exposure zone 36, and the two predrying nozzles 43 correspond to the other two container stop positions at the downstream side. The drying zone 37 has four main drying hot air nozzles 44 in corresponding relation with four container stop positions. The preheating hot air nozzles 41, predrying hot air nozzles 43 and main drying hot air nozzles 44 have connected thereto hot air supply pipes 45, 46, 47, respectively, which extend from an unillustrated hot air source.

A positive-pressure air duct 51 has outlets connected to the right side wall of the disinfection chamber 12 in communication with the preheating zone 35 and the drying zone 37, respectively. An exhaust duct 52 has inlets connected to the left side wall of the chamber 12 in communication with the exposure zone 36 and the drying zone 37. The exhaust duct 52 has an outlet connected to the suction side of a blower 53.

The outlets of the air duct 51 and the inlets of the exhaust duct 52 are each provided with a semicircular damper 54 for pressure regulation. The dampers 54 are suitably sized so as to give a higher internal pressure to the preheating zone 35 and the drying zone 37 than to the exposure zone 36, whereby air is caused to flow from the preheating zone 35 and the drying zone 37 toward the exposure zone 36.

The antiseptic supply device 13 comprises a hydrogen peroxide solution tank 61, a metering tube pump 62 connected at its suction side to the tank 61, vertical rodlike dropping nozzles 63 connected to the discharge side of the pump 62, a gasification tank 65 surrounding the lower-end spouts of the nozzles 63 and housing a heater 64, a carrier air duct 67 having an outlet connected to the gasification tank 65 and an inlet connected to an air heater 56, and a hydrogen peroxide gas supply pipe 68 having an inlet connected to the tank 65 and an outlet connected to the hydrogen peroxide gas nozzles 42.

Hot air is forced into the preheating zone 35 through the preheating nozzles 41, whereby the containers C brought into the preheating zone 35 are heated to a surface temperature of 40 to 80 deg C. An aqueous hydrogen peroxide solution is sent from the tank 61 to the gasification tank 55 by the pump 62, then applied dropwise onto the heater 64 and thereby converted to a gas. The hydrogen peroxide gasified within the tank 65 is transported by carrier air to the nozzles 42, from which the gas is injected into the exposure zone 36. The gas injected comes into contact with the surfaces of the containers brought into the exposure zone 36 and is condensed thereon. On the other hand, hot air is injected into the exposure zone 36 via the predrying nozzles 43, whereby the peroxide condensate on the container surfaces is heated to some extent for predrying. The predried containers C are brought into the drying zone 37. Hot air is injected into the drying zone 37 through the main drying nozzles 44. In the drying zone 37, the hydrogen peroxide is rapidly removed by drying from the surfaces of the containers C brought in as preheated and predried.

The apparatus described was tested for disinfection effect (bactericidal effect) by the method to be described below.

The containers used were 1,000-ml cartons. Spores of *B. subtilis* were applied to the inner surfaces of the containers. A 35% aqueous solution of hydrogen peroxide was gasified at a rate of 15 ml/min and then applied to some of the containers for 0.9 sec, followed by drying for 2.7 sec for the removal of the peroxide. The cartons thus treated for disinfection were used as samples, and those not subjected to the disinfection treatment as blanks. The bactericidal effect was calculated from the following equation based on comparison between the samples and the blanks.

Bactericidal effect=$\log_{10}$ (A/B) wherein A is the average number of spores of the blank, and B is the average number of survivors of the sample.

The test result is as follows.

| Preheating | Preheating temp. | Bactericidal effect |
|---|---|---|
| No | Room temp. | 1.5 |
| Yes | 40 deg C. | 2.2 |
| Yes | 80 deg C. | 2.2 |

As will be apparat from the above result, the preheating conducted achieved a greater bactericidal effect, while the difference in preheating temperature produced no change in the effect.

To substantiate the effect of preheating, an experiment was conducted in the laboratory instead of using the apparatus.

Spores of the same species as above were applied to test pieces of plastic, which were then preheated by a suitable method, thereafter exposed for 1.0 sec to hydrogen peroxide gas prepared by gasifying a 35% aqueous solution of hydrogen peroxide at a rate of 15 ml/min, and subsequently dried for 2.7 sec for the removal of the peroxide. The test result is given below.

| Preheating | Preheating temp. | Bactericidal effect |
|---|---|---|
| No | Room temp. | 1.1 |
| Yes | 40 deg C. | 4.6 |
| Yes | 80 deg C. | 4.6 |

The result reveals that the preheating achieved a greater affect as is the case with the apparatus. The test, in which the sample was not in the form of a container, indicates that preheating is effective also for disinfecting a packaging material in the form of a sheet.

Another test was conducted using a mist of hydrogen peroxide in place of hydrogen peroxide gas.

Under the same condition as above, spores were applied to 1,000-ml cartons as samples. A 3.5% aqueous solution of hydrogen peroxide was made into a mist at a rate of 10 ml/min using atomizing nozzles or a supersonic generator, and the mist was sprayed onto the cartons for 1.2 sec, followed by drying for 7.2 sec for the removal of the peroxide.

| Preheating | Preheating temp. | Bactericidal effect |
|---|---|---|
| No | Room temp. | 2.1 |
| Yes | 40 deg C. | 2.5 |
| Yes | 80 deg C. | 2.6 |

The test shows that the use of the hydrogen peroxide mist produced a somewhat lower bactericidal effect and required a longer period of drying time, but that the preheating was effective. The test further indicates that the higher preheating temperature resulted in a higher bactericidal effect.

What is claimed is:

1. An apparatus for disinfecting containers comprising a disinfection chamber surrounding a section of a container transport path, partition means for dividing the interior of the disinfection chamber into a preheating zone, an exposure zone and a drying zone as arranged downstream from an upstream side of the transport path, antiseptic supply means for supplying hydrogen peroxide gas or mist to the exposure zone, and means for supplying hot air to the preheating zone and the drying zone, wherein the drying zone and the preheating zone are each maintained at a higher internal pressure than the exposure zone.

2. An apparatus as defined in claim 1, further comprising a positive-pressure air duct having outlets connected to the preheating zone and the drying zone, respectively, and an exhaust duct having inlets connected to the exposure zone and the drying zone, respectively.

* * * * *